US007655256B2

(12) United States Patent
Hughes

(10) Patent No.: US 7,655,256 B2
(45) Date of Patent: *Feb. 2, 2010

(54) PHARMACEUTICAL FORMULATION INCLUDING A RESINATE AND AN AVERSIVE AGENT

(75) Inventor: Lyn Hughes, Harleysville, PA (US)

(73) Assignee: Rohm and Haas Company, Philadelphia, PA (US)

( * ) Notice: Subject to any disclaimer, the term of this patent is extended or adjusted under 35 U.S.C. 154(b) by 1123 days.

This patent is subject to a terminal disclaimer.

(21) Appl. No.: 10/679,785

(22) Filed: Oct. 6, 2003

(65) Prior Publication Data

US 2004/0126324 A1 Jul. 1, 2004

Related U.S. Application Data

(63) Continuation-in-part of application No. 10/016,336, filed on Nov. 2, 2001, now abandoned.

(60) Provisional application No. 60/322,624, filed on Sep. 17, 2001.

(51) Int. Cl.
*A61K 9/48* (2006.01)
*A61K 9/20* (2006.01)

(52) U.S. Cl. ........................ 424/454; 424/465

(58) Field of Classification Search ........................ None
See application file for complete search history.

(56) References Cited

U.S. PATENT DOCUMENTS

| | | | |
|---|---|---|---|
| 3,268,577 A | 8/1966 | Hay | |
| 3,773,955 A | 11/1973 | Pachter at al. | 424/260 |
| 3,966,940 A | 6/1976 | Pachter et al. | 424/260 |
| 3,980,766 A | 9/1976 | Shaw et al. | 424/10 |
| 4,070,494 A | 1/1978 | Hoffmeister et al. | 424/2 |
| 4,457,933 A | 7/1984 | Gordon et al. | 424/260 |
| 4,529,583 A | 7/1985 | Porter | 424/10 |
| 4,599,342 A * | 7/1986 | LaHann | 514/282 |
| 5,334,378 A * | 8/1994 | Mitani et al. | 424/78.1 |
| 6,228,863 B1 | 5/2001 | Palermo | 514/282 |
| 7,332,182 B2 * | 2/2008 | Sackler | 424/452 |

FOREIGN PATENT DOCUMENTS

| | | |
|---|---|---|
| EP | 0 709 098 | 5/1996 |
| GB | 862 242 | 3/1961 |
| GB | 2 331 702 | 6/1999 |
| GB | 2 358 585 | 8/2001 |
| JP | 05279245 A | 10/1993 |
| WO | 90 / 04965 | 5/1990 |
| WO | 91/07950 | 6/1991 |
| WO | 95/20947 | 8/1995 |
| WO | 00/33835 | 6/2000 |
| WO | 01/08661 | 2/2001 |
| WO | 02/094254 | 11/2002 |
| WO | 03 / 013476 | 2/2003 |

OTHER PUBLICATIONS

Page, Henry A.S., "Bitrex—a bitter solution to safety," *Chemistry and Industry* (London) Nov. 21, 1988, pp. 721-723.
Smith, R.L. *Ecology and Field Biology*, third edition, published by Harper and Row, 1980 p. 562.
Porter, Stuart C., "Coating of Pharmaceutical Dosage Forms," Chapter 46 of *Remington: The Science and Practice of Pharmacy*, 20th edition, by Alfonso R. Gennary, published by Lippincott Williams & Wilkins, 2003.
Glenn, M., "Hillbilly Heroin," *Houston Chronicle*, Aug. 7, 2001.
Rudnic, M.R. et. al, "Oral Solid Dosage Forms," Chapter 45 of *Remington: The Science and Practice of Pharmacy*, 20th edition, by Alfonso R. Gennary, published by Lippincott Williams & Wilkins, 2003.
Kalb, C., "Playing With Pain Killers," *Newsweek*, Apr. 9, 2001, p. 44.
Rosenberg, D., "How One Town Got Hooked," *Newsweek*, Apr. 9, 2001, p. 48.
Merck Index, 13th edition, 2001, published by Merck & Co., Whitehouse Station, NJ, USA, p. 296.

* cited by examiner

*Primary Examiner*—Carlos A Azpuru
(74) *Attorney, Agent, or Firm*—Tifani M. Cottingham

(57) ABSTRACT

The present invention provides a pharmaceutical that includes, in combination, a resinate and an aversive agent. The resinate includes an ion exchange resin and an drug. The drug is a controlled substance. In variants of the invention, both the aversive agent and the controlled substance are loaded onto the ion exchange resin; the aversive agent is loaded onto the ion exchange resin, and the controlled substance is not loaded onto the ion exchange resin; the controlled substance is loaded onto the ion exchange resin, and the aversive agent is not loaded onto the ion exchange resin; or, the controlled substance is loaded onto a first ion exchange resin, and the aversive agent is loaded onto an ion exchange resin different from the first ion exchange resin.

8 Claims, No Drawings

PHARMACEUTICAL FORMULATION INCLUDING A RESINATE AND AN AVERSIVE AGENT

CROSS REFERENCE TO RELATED PATENT APPLICATIONS

This is a continuation-in-part application of prior U.S. application Ser. No. 10/016,336 filed Nov. 2, 2001, now abandoned which is a continuation-in-part of prior pending U.S. provisional application Ser. No. 60/322,624 filed Sep. 17, 2001.

This application claims benefit to U.S. patent application Ser. No. 10/016,336, filed Nov. 2, 2001, entitled: "Dosage Forms."

BACKGROUND

Abuse of controlled substances is a serious and growing problem throughout the world. For example, the abuse of an extended release form of oxycodone has been the recent subject of many articles such as 'Playing With Pain Killers' and 'How One Town Got Hooked'. See, Newsweek, Apr. 9, 2001, pages 45-51. Further, The New York Times profiled the problem of oxycodone abuse by inhalation of the crushed pill. See, The New York Times, Jul. 29, 2001. It is estimated that in America four million people over the age of 12 used prescription painkillers and stimulants for non-medical reasons in the space of just one month, approximately half of them saying they'd done it for the first time. Emergency room visits related to such abuse approximately doubled between 1992 and 1999.

There are three main routes that drug abusers use for administering the drug substances: parenteral, oral, and inhalation. The parenteral route is commonly called 'mainlining' and requires the drug substance to be in solution such that it can be injected intravenously with a syringe. For solid dosage form drugs this requires some type of extraction and concentration procedure to render the drug substance suitable for injection. Inhalation of a solid drug substance through the nose is commonly called 'snorting'. For solid dosage form drugs this requires only that the dosage form be crushed into a powder, or emptied from a capsule. Breathing in vapors is frequently known as 'huffing'. Both snorting and huffing result in the rapid absorption of the drug substance through the mucosa of the respiratory system.

The potential for abuse is increased by the use of extended release formulations because they typically contain more than the immediate release single dose of active ingredient. Circumventing the extended release mechanism delivers the full dose, which is intended to be delivered over a longer time period, immediately. For example, crushing an extended release oxycodone tablet separates a gelling matrix from the oxycodone active ingredient, such that when inhaled through the nose the gelling matrix cannot exert the extended release effect. Similarly it is sometimes possible to circumvent the extended release effect by chewing the dosage form.

There exists a need in the art for a pharmaceutical which will greatly reduce the ability of abusers to abuse various drugs.

The term "therapeutic concentration" as used herein means the concentration of the pharmaceutically active ingredient in the blood plasma that is obtained by the administration of the recommended doses using the prescribed method of administration. Recommended doses for Schedule II-V controlled substances are defined in the literature. For example, see 'Drug Facts and Comparisons', published by Facts and Comparisons, St Louis.

The term "high," as used herein means the non-therapeutic effect desired by drug addicts and recreational drug users The term "mucosal membrane" as used herein means any mucosal membrane of the body through which an active substance can be administered, including, but not limited to, nasal, lingual, buccal, pharyngeal, bronchial, rectal, urethral and vaginal.

The term "respiratory mucosal membrane" as used herein means the mucous membrane lining the nasal and pharyngeal cavities, the bronchial tubes, and the lungs. Typically, snorting into the nasal cavity is the common, preferred route of abuse for a solid oral dosage form which has been crushed by one intending to inhale said crushed dosage form to obtain the high.

The term "illicit extracts" as used herein are those extracts obtained by any of the means known to drug addicts, drug users, and recreational drug users for extracting an active substance from an oral dosage form. In the interests of social responsibility these methods will not be described herein.

The term "sensory agent" as used herein means those agents that modify ones sensory perception of the dosage form.

The term "meq/g", as used herein, refers to the fact that ion exchange resins are characterized by their capacity to exchange ions. This is expressed as the "Ion Exchange Capacity." For cation exchange resins the term used is "Cation Exchange Capacity," and for anion exchange resins the term used is "Anion Exchange Capacity." The ion exchange capacity is measured as the number equivalents of an ion that can be exchanged and can be expressed with reference to the mass of the polymer (herein abbreviated to "Weight Capacity") or its volume (often abbreviated to "Volume Capacity"). A frequently used unit for weight capacity is "milliequivalents of exchange capacity per gram of dry polymer." This is commonly abbreviated to "meq/g."

The term "respiratory irritant' as use herein means substances that cause irritation when administered to the respiratory mucosal membrane. Said irritation can include, but is not limited to, coughing, dyspnea, rhinitis, nasal congestion, eye irritation, lachrymation, and sneezing.

When describing dosage forms the term "immediate release" as used herein means a dosage form from which the active ingredient is dissolved as quickly as possible after administration. In the pharmaceutical arts said immediate release dosage forms are frequently referred to as "conventional" dosage forms.

When describing dosage forms the term "modified release" as used herein means a dosage form whose drug-release characteristics of time course and/or location are chosen to accomplish therapeutic or convenience objectives not offered by conventional dosage forms. Said modified release dosage forms include dosage forms commonly known in the art as, delayed, sustained, extended, targeted, prolonged, pulsatile, zero-order, constant rate, and controlled.

The term "aversive response" as used herein means a response in a person, resulting from administration of a dosage form containing a controlled substance, via any of the known routes of administration, sufficiently unpleasant that said person decides not to administer said dosage form by the same route of administration again The term "aversive agent" as used herein means any substance that is included in a dosage form that creates an aversive response.

The term "nociceptive" as used herein means a response characterized by pain. For example the term 'nociceptive efficacy' when applied to an irritant refers to the quantification of the ability of said irritant to cause pain.

The present invention provides a pharmaceutical that includes, in combination, a resinate and an aversive agent. The resinate includes an ion exchange resin and an drug. The drug is a controlled substance. In variants of the invention, both the aversive agent and the controlled substance are loaded onto the ion exchange resin; the aversive agent is loaded onto the ion exchange resin, and the controlled substance is not loaded onto the ion exchange resin; the controlled substance is loaded onto the ion exchange resin, and the aversive agent is not loaded onto the ion exchange resin; or, the controlled substance is loaded onto a first ion exchange resin, and the aversive agent is loaded onto an ion exchange resin different from the first ion exchange resin.

In another variant, the present invention relates to an oral pharmaceutical dosage form not susceptible to abuse by respiratory mucosal membrane administration comprising one or more aversive agents, and one or more resinates.

A respiratory irritant such as powdered chili peppers, or concentrated extracts of such products that contain capsaicin or capsaicin-like components, is incorporated into the solid oral dosage form of the controlled substance. When the oral dosage form is used as prescribed, i.e. swallowed whole, said irritant causes no aversive response. However, if the oral dosage form is rendered into a powder and inhaled, said irritant creates intense discomfort in the user, including coughing, dyspnea, rhinitis, nasal congestion, eye irritation, lachrymation, and sneezing. This intense discomfort has the effect of deterring people from using said inhalation route as a means of administration, i.e. it elicits an aversive response.

A bitter tasting agent such as denatonium benzoate (Bitrex®) or a sour tasting agent such as citric acid, is incorporated into the solid oral dosage form of the controlled substance. When the oral dosage form is used as prescribed, i.e. swallowed whole, said bitter or sour substance causes no aversive response. However, if the oral dosage form is chewed, said bitter or sour substance creates an intensely unpleasant taste. This unpleasant taste has the effect of deterring people from chewing the dosage form, i.e. it elicits an aversive response.

The Controlled Substances Act of 1970 regulates the manufacturing, distribution, and dispensing of drugs that have abuse potential. The Drug Enforcement Agency (DEA) within the US Department of Justice is the chief agency responsible for enforcing said act. Drugs under the jurisdiction of said Act are divided into five schedules (I thru V) based on their medical utility, potential for abuse, and physical and psychological dependence. Schedule I substances have high abuse potential and no accepted medical use. Schedule II also have high abuse potential, but also have medical utility. Schedules III, IV, and V have progressively lower abuse potential.

Because the DEA rates abuse potential based on specific dosage forms it is not uncommon for a drug to be rated in multiple schedules. For example codeine appears as Schedule II, Schedule III, and Schedule IV, depending on the specific dosage form and dosage amount. To avoid duplication in the list of controlled substance below, multiple occurrences have been removed and any controlled substance that had multiple occurrences is placed in the highest abuse potential category for which is has been scheduled. For example, codeine has been included as Schedule II, but not Schedule III or Schedule IV. This is not intended to limit the scope of the invention. The utility of the Applicant's invention lies in the fact that any controlled substance, regardless of what schedule it appears on, is suitable for formulating into the Applicant's dosage form.

Controlled substances useful in the practice of the invention are those categorized by the DEA as Schedule II, III, IV, and V controlled substances.

Schedule II substances include, but are not limited to, 1-1-Phenylcyclohexylamine, 1-Piperidinocyclohexanecarbonitrile, Alfentanil, Alphaprodine, Amobarbital, Amphetamine, Anileridine, Benzoylecgonine, Bezitramide, Carfentanil, Coca Leaves, Cocaine, Codeine, Dextropropoxyphene, Dihydrocodeine, Diphenoxylate, Diprenorphine, Ecgonine, Ethylmorphine, Etorphine HCl, Fentanyl, Glutethimide, Hydrocodone, Hydromorphone, Isomethadone, Levo-alphacetylmethadol, Levomethorphan, Levorphanol, Meperidine, Meperidine intermediate-A, Meperidine intermediate-B, Meperidine intermediate-C, Metazocine, Methadone, Methadone intermediate, Methamphetamine, Methylphenidate, Metopon, Moramide-intermediate, Morphine, Nabilone, Opium extracts, Opium fluid extract, Opium poppy, Opium tincture, Opium, granulated, Opium, powdered, Opium, raw, Oxycodone, Oxymorphone, Pentobarbital, Phenazocine, Phencyclidine, Phenmetrazine, Phenylacetone, Piminodine, Poppy Straw, Poppy Straw Concentrate, Racemethorphan, Racemorphan, Remifentanil, Secobarbital, Sufentanil, Thebaine Schedule III substances include, but are not limited to, Amobarbital, Anabolic steroids, Aprobarbital, Barbituric acid derivative, Benzphetamine, Boldenone, Butabarbital, Butalbital, Chlorhexadol, Chlorotestosterone, Chlorphentermine, Clortermine, Clostebol, Codeine, Dehydrochlormethyltestosterone, Dihydrocodeine, Dihydrotestosterone, Dronabinol, Drostanolone, Ethylestrenol, Ethylmorphine, Fluoxymesterone, Formebolone, Hydrocodone, Ketamine, Lysergic acid, Lysergic acid amide, Mesterolone, Methandienone, Methandranone, Methandriol, Methandrostenolone, Methenolone, Methyltestosterone, Methyprylon, Mibolerone, Morphine, Nalorphine, Nandrolone, Norethandrolone, Oxandrolone, Oxymesterone, Oxymetholone, Pentobarbital, Phendimetrazine, Secobarbital, Stanolone, Stanozolol, Sulfondiethylmethane, Sulfonethylmethane, Sulfonmethane, Talbutal, Testolactone, Testosterone, Thiamylal, Thiopental, Tiletamine, Trenbolone, Vinbarbital.

Schedule IV substances include, but are not limited to, Alprazolam, Barbital, Bromazepam, Butorphanol, Camazepam, Cathine, Chloral betaine, Chloral hydrate, Chlordiazepoxide, Clobazam, Clonazepam, Clorazepate, Clotiazepam, Cloxazolam, Cocaine, Delorazepam, Dexfenfluramine, Dextropropoxyphene, Diazepam, Diethylpropion, Difenoxin, Estazolam, Ethchlorvynol, Ethinamate, Ethyl loflazepate, Fencamfamin, Fenfluramine, Fenproporex, Fludiazepam, Flunitrazepam, Flurazepam, Halazepam, Haloxazolam, Ketazolam, Loprazolam, Lorazepam, Lormetazepam, Mazindol, Mebutamate, Medazepam, Mefenorex, Meprobamate, Methohexital, Methylphenobarbital, Midazolam, Modafinil, Nimetazepam, Nitrazepam, Nordiazepam, Oxazepam, Oxazolam, Paraldehyde, Pemoline, Pentazocine, Petrichloral, Phenobarbital, Phentermine, Pinazepam, Pipradrol, Prazepam, Quazepam, Sibutramine, Temazepam, Tetrazepam, Triazolam, Zaleplon, Zolpidem Schedule V substances include, but are not limited to Buprenorphine, Difenoxin, Dihydrocodeine, Diphenoxylate, Pyrovalerone.

Aversive agents useful in the practice of this invention include, but are not limited to, respiratory irritants, bitter substances, and sour substances. Aversive agents useful in the practice of this invention are solids in one variant. The solid can be the agent in pure form or a solid containing the agent. Aversive agents useful in the practice of this invention are of natural or synthetic origin. One aspect of this invention is the use of capsaicinoids as an aversive agent which acts as a respiratory irritant to create an aversive response. Capsaicinoids are alkaloid substances which occur naturally in the fruit of various chile pepper plants. The principal capsaicinoids found in most pepper plants are capsaicin, dihydrocapsaicin, capsico, and capsacutin. The principal capsaicinoid is capsaicin. There can be multiple capsaicinoids in one pepper and different peppers have different concentrations of capsaicinoids. The production of capsaicinoids is a form of chemical defense against being eaten and thus acts naturally as an animal repellant. See, Smith, R. L., Ecology and Field Biology, p. 562 (3d Ed. 1980). Capsaicinoids are the chemicals responsible for the "hot" sensation associated with peppers. The hotness of the various capsicums is directly attributable to their capsaicinoid content. Capsaicinoids generate a spicy flavor in the mouth but are irritants when applied to mucous membranes.

Capsicum is the formal term used to refer to the dried ripe fruit of the various species of chili peppers.

Therapeutically, capsaicin is listed as a counterirritant (Merck Index, 9th Ed., p. 224). Capsicum has Generally Regarded as Safe (GRAS) status in the USA. Capsaicin, capsicum, and capsicum oleoresin have monographs in the US Pharmacopeia 24.

Respiratory irritants useful in the practice of this invention include, but are not limited to, pure compounds and mixtures of capsaicin, capsico, capsacutin, dihydrocapsaicin, nordihydrocapsaicin, homocapsaicin, homodihydrocapsaicin, capsaicinoids, gingerol, chemical mace, piperine, isochavicine, isopiperine, piperidine, chavicine, piperettine, zingerone, shogaol, valleral, isovallerals, vanyllylamide, nonoyl vanyllamide, vanyllylamide derivatives, synthetic derivatives of capsaicinoids, and extracts, capsicums, and powders of, *Capsicum frutescens* varieties, *Capsicum anuum* varieties, *Capsicum chinense* varieties, *Capsicum baccatum* varieties, *Capsicum pubescens* varieties, *Capsicum* species, *Piper migrum* varieties, *Piper longum* varieties, *Piper retrofractum* varieties, *Piper officinarum* varieties, *Piperaceae* species, *Brassica juncea* varieties, *Brassica. nigra* varieties, *Sinapis alba* varieties, *Sinapis arvensis* varieties, *Zingiber officinale* varieties, and *Lactarius vellereus* varieties and mixtures thereof Respiratory irritants useful in the practice of the invention are pure compounds and mixtures of capsaicin, capsico, capsacutin, dihydrocapsaicin, nordihydrocapsaicin,homocapsaicin, homodihydrocapsaicin, capsaicinoids, gingerol, chemical mace, piperine, isochavicine, isopiperine, piperidine, chavicine, piperettine, zingerone, shogaol, valleral, isovallerals, vanyllylamide, nonoyl vanyllamide, vanyllylamide derivatives, synthetic derivatives of capsaicinoids, and extracts, capsicums, and powders of, *Capsicum frutescens* varieties, *Capsicum anuum* varieties, *Capsicum chinense* varieties, *Piper migrum* varieties, *Piper longum* varieties, *Piper retrofractum* varieties, *Piper officinarum* varieties, *Brassica juncea* varieties, *Brassica. nigra* varieties, *Sinapis alba* varieties, *Sinapis arvensis* varieties, and *Zingiber officinale* varieties and mixtures thereof.

Respiratory irritants useful in the practice of the invention are pure compounds and mixtures of capsaicin, capsico, capsacutin dihydrocapsaicin, nordihydrocapsaicin,homocapsaicin, homodihydrocapsaicin, capsaicinoids, gingerol, piperine, isopiperine, piperidine, piperettine, zingerone, shogaol, valleral, isovallerals, vanyllylamide, vanyllylamide derivatives, and extracts, capsicums, and powders of, *Capsicum frutescens* varieties, *Capsicum anuum* varieties, *Capsicum chinense* varieties, *Piper migrum* varieties, *Piper longum* varieties, *Piper retrofractum* varieties, *Piper officinarum* varieties, *Brassica juncea* varieties, *Brassica. nigra* varieties, *Sinapis alba* varieties, *Sinapis arvensis* varieties, and *Zingiber officinale* varieties and mixtures thereof Respiratory irritants useful in the practice of the invention are pure compounds and mixtures of capsaicin, capsacutin dihydrocapsaicin, nordihydrocapsaicin, homocapsaicin, homodihydrocapsaicin, capsaicinoids, gingerol, piperine, isopiperine, zingerone, shogaol, and vanyllylamide derivatives and mixtures thereof.

The use of capsaicin with cocaine is contra-indicated.

The amount of respiratory irritant useful in the practice of this invention is that which is sufficient to elicit an aversive response in the user when said irritant is inhaled through the respiratory mucosa but that which is not sufficient to elicit an aversive response or an adverse medical response in the user when said irritant is swallowed as a solid oral dosage form in the manner prescribed.

The nociceptive efficacy of the respiratory irritants varies greatly depending both on chemical structure of the active ingredient of said irritant, and the amount of active ingredient in said irritant. The following amounts of respiratory irritants are provided as examples. Effective amounts of other respiratory irritants can be determined using techniques well known to those skilled in the art.

The amount of the respiratory irritants capsaicin and dihydrocapsaicin is a combined total of 0.002-100 mg per dose in one variant of the invention.

The amount of the respiratory irritant zingerone is optionally 0.04-200 mg per dose.

The amount of the respiratory irritant shogaol is optionally 0.04-200 mg per dose The amount of the respiratory irritant piperine is optionally 0.04-200 mg per dose The amount of the respiratory irritants capsicums of *Capsicum annum, Capsicum frutescens*, and *Capsicum chinense* is optionally 0.1-450 mg per dose.

The amount of the respiratory irritants capsaicin and dihydrocapsiacin is optionally a combined total of 0.004-25 mg per dose.

The amount of the respiratory irritant zingerone is optionally 0.2-150 mg per dose.

The amount of the respiratory irritant shogaol is optionally 0.2-150 mg per dose.

The amount of the respiratory irritant piperine is optionally 0.2-150 mg per dose.

The amount of the respiratory irritants capsicums of *Capsicum annum, Capsicum frutescens*, and *Capsicum chinense* is optionally 0.4-350 mg per dose.

The amount of the respiratory irritants capsaicin and dihydrocapsiacin is optionally a combined total of 0.02-15 mg per dose.

The amount of the respiratory irritant zingerone is optionally 0.2-100 mg per dose.

The amount of the respiratory irritant shogaol is optionally 0.2-100 mg per dose.

The amount of the respiratory irritant piperine is optionally 0.2-100 mg per dose.

The amount of the respiratory irritants capsicums of *Capsicum annum, Capsicum frutescens*, and *Capsicum chinense* is optionally 0.6-250 mg per dose.

Bitter agents also create an aversive response. The use of bitter agents is particularly useful in preventing abuse of controlled substances by chewing the oral dosage form. Bitter agents useful in the practice of this invention include, but are not limited to, agaricic acid, benzyl acetate, brucine, brucine sulfate, caffeine, capsaicin, catechin, dadzein, denatonium benzoate (Bitrex®) and other denatonium salts, denatonium capsaicinate, denatonium chloride, denatonium saccharide, diethyl phthalate, epicatechin, genistein, gentian violet, gerianol, hydroxytyrosol, kashin, limonin, linalool, linalool acetate, methyl anthranilate, naringin, nobiletin, oleuropin, phenylethyl alcohol, polyphenols, quassin, quebracho, quercitin, quinine, quinine sulfate, quinine hydrochloride, sinensetin, sucrose benzoate, sucrose octaacetate, and tangeretin and mixtures thereof.

Bitter agents useful in the practice of this invention are, denatonium benzoate (Bitrex®) and other denatonium salts, denatonium capsaicinate, denatonium chloride, denatonium saccharide, limonin, linalool, linalool acetate, naringin, quassin, quercitin, sucrose benzoate, and sucrose octaacetate and mixtures thereof.

Bitter agents useful in the practice of this invention are denatonium benzoate (Bitrex®), denatonium capsaicinate, denatonium saccharide, and sucrose octaacetate and mixtures thereof.

Further, sour agents also create an aversive response. The use of sour agents is particularly useful in preventing abuse of controlled substances by chewing the oral dosage form. Sour agents useful in the practice of this invention include, but are not limited to, acidic organic compounds that contain one or more acidic protons per molecule and mixtures thereof.

Sour agent useful in the practice of the invention are acidic organic compounds that contain two or more acidic protons per molecule and mixtures thereof.

Sour agents useful in the practice of the invention are citric acid and tartaric acid and mixtures thereof.

The controlled substance and aversive agent are incorporated into the dosage form using any of the methods known in the art for preparation of solid oral dosage forms. See, Remington's Pharmaceutical Sciences, 16$^{th}$ Edition.

Further, different combinations of aversive agents can be combined in the same dosage form. For example, if it is desired to reduce the potential for abuse via both inhalation and chewing, it may be desirable to combine both a respiratory irritant and a bitter agent in the same formulation. Further, combination of averise agents can sometimes have a synergistic effect, such that the combination has a greater effect than the sum of the individuals taken separately. Still further, people have different responses to taste, such that a mixture of bitter agents may be needed to be effective in a larger fraction of the population.

In addition to the controlled substance and aversive agent, excipients are used in the manufacture of the oral dosage forms of the present invention. Excipients useful in the practice if this invention include but are not limited to preservatives, viscosity agents, fillers, lubricants, glidants, disintegrants, binders, and encapsulants.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0-2% preservatives.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0-25% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0-75% fillers.

Preferred lubricants include, but are not limited to, magnesium stearate, stearic acid, and talc. The pharmaceutical compositions of the present invention include 0-2% lubricants.

Preferred glidants include, but are not limited to, talc and colloidal silica. The compositions of the present invention include from 0-5% glidants.

Preferred disintegrants include, but are not limited to, starch, sodium starch glycolate, crospovidone, croscarmelose sodium, polacrilin potassium, and microcrystalline cellulose. The pharmaceutical compositions of the present invention include from 0-30% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 0.1-10% binders.

Encapsulants useful in the practice of the present invention include, but are not limited to permable coatings, impermeable coatings, and matrices.

Permeable coatings useful in this invention are well know to one skilled in the art and include Eudragit® RL, and Eudragit® RS (Rohm-Pharma Darmstadt, Germany)

Non-permeable coatings useful in this invention are well known to one skilled in the art and include Aquacoat CPD (FMC Corporation, Philadelphia, Pa., USA), Eudragit® E100, Eudragit® L100, Eudragit® S100 (Rohm-Pharma Darmstadt, Germany), Kollicoat® MA 30 DP (BASF Aktiengesellschaft, Ludwigshafen, Germany), Opadry light pink.

Plastizers for use with coatings useful in the practice of the invention include but are not limited to, triethyl citrate, 1,2-propylene glycol, polyethylene glycols, and tracetin.

Matrices for encapsulation useful in the practice of the invention include, but are not limited to, anion exchange resins, cation exchange resins, polymeric adsorbents, carbonaceous adsorbents, cellulosic polymers, and acrylic polymers.

Dosage forms of the present invention are immediate release or modified release.

Specifically, the dosage form of the present invention renders the controlled substance unable to deliver the desired non therapeutic effect, i.e., the high.

The utility of the invention lies in the fact that the rate of release of the controlled substance is not affected by crushing the solid oral dosage form, or of emptying the dosage from a capsule, and the fact that there is an aversive agent also used in the invention. For example, when said solid oral dosage form is crushed and inhaled, chewed or illicitly extracted and injected for non-therapeutic purposes the controlled substance is not available for total release, but will release at a rate that does not result in a plasma concentration that exceeds the therapeutic concentration. The high is not obtained at the therapeutic concentration.

The Controlled Substances Act of 1970 regulates the manufacturing, distribution, and dispensing of drugs that have abuse potential. The Drug Enforcement Agency (DEA)

within the US Department of Justice is the chief agency responsible for enforcing said act. Drugs under the jurisdiction of said Act are divided into five schedules (I thru V) based on their medical utility, potential for abuse, and physical and psychological dependence. Schedule I substances have high abuse potential and no accepted medical use. Schedule II also have high abuse potential, but also have medical utility. Schedules III, IV, and V have progressively lower abuse potential.

Because the DEA rates abuse potential based on specific dosage forms it is not uncommon for a drug to be rated in multiple schedules. For example codeine appears as Schedule II, Schedule III, and Schedule IV, depending on the specific dosage form and dosage amount. To avoid duplication in the list of controlled substance below, multiple occurrences have been removed and any controlled substance that had multiple occurrences is placed in the highest abuse potential category for which is has been scheduled. For example, codeine has been included as Schedule II, but not Schedule III or Schedule IV. This is not intended to limit the scope of the invention. The utility of the Applicant's invention lies in the fact that any ionizable controlled substance, regardless of what schedule it appears on, is suitable for formulating into the Applicant's dosage form.

Controlled substances useful in the practice of the invention are those categorized by the DEA as Schedule II, III, IV, and V controlled substances. Controlled substances useful in the practice of the invention must be ionizable such that a controlled substance-ion exchange resin complex can be formed.

Schedule II substances include, but are not limited to, 1-Phenylcyclohexylamine, 1-Piperidinocyclohexanecarbonitrile, Alfentanil, Alphaprodine, Amobarbital, Amphetamine, Anileridine, Benzoylecgonine, Bezitramide, Carfentanil, Cocaine, Codeine, Dextropropoxyphen, Dihydrocodeine, Diphenoxylate, Diprenorphine, Ecgonine, Ethylmorphine, Etorphine HCl, Fentanyl, Glutethimide, Hydrocodone, Hydromorphone, Isomethadone, Levo-alphacetylmethadol, Levomethorphan, Levorphanol, Meperidine, Metazocine, Methadone, Methamphetamine, Methylphenidate, Metopon, Morphine, Nabilone, Oxycodone, Oxymorphone, Pentobarbital, Phenazocine, Phencyclidine, Phenmetrazine, Piminodine, Racemethorphan, Racemorphan, Remifentanil, Secobarbital, Sufentanil, Thebaine Schedule III substances include, but are not limited to, Aprobarbital, Barbituric acid derivative, Benzphetamine, Butabarbital, Butalbital, Chlorphentermine, Ketamine, Lysergic acid, Lysergic acid amide, Nalorphine, Phendimetrazine, Talbutal, Thiamylal, Thiopental, Vinbarbital.

Schedule IV substances include, but are not limited to, Alprazolam, Barbital, Bromazepam, Butorphanol, Camazepam, Cathine, Chloral, Chlordiazepoxide, Clobazam, Clonazepam, Clorazepate, Clotiazepam, Cloxazolam, Delorazepam, Dexfenfluramine, Diazepam, Diethylpropion, Difenoxin, Estazolam, Ethyl loflazepate, Fencamfamin, Fenfluramine, Fenproporex, Fludiazepam, Flunitrazepam, Flurazepam, Halazepam, Haloxazolam, Ketazolam, Loprazolam, Lorazepam, Lormetazepam, Mazindol, Medazepam, Mefenorex, Methohexital, Methylphenobarbital, Midazolam, Nimetazepam, Nitrazepam, Nordiazepam, Oxazepam, Oxazolam, Pemoline, Pentazocine, Phenobarbital, Phentermine, Pinazepam, Pipradrol, Prazepam, Quazepam, Sibutramine, Temazepam, Tetrazepam, Triazolam, Zaleplon, Zolpidem.

Schedule V substances include, but are not limited to, Buprenorphine, Difenoxin, Pyrovalerone.

Preferred controlled substances useful in the practice of the invention are those categorized by the DEA as Schedule II, III, and IV controlled substances.

More preferred controlled substance useful in the practice of the invention are those categorized by the DEA as Schedule II and III controlled substances.

controlled substance useful in the practice of the invention are those categorized by the DEA as Schedule II controlled substances. The Schedule II substance is oxycodone.

The oral dosage form of the present invention is prepared by making a complex of a controlled substance and an ion exchange resin and formulating said complex into an oral dosage form.

The controlled substance-ion exchange resin complex can by formulated into any of the oral dosage forms known in the art including, but not limited to, powders, tablets, pills, and capsules.

The controlled substance-ion exchange resin complex can be prepared by any of the methods known in the art. The typical method, known to those skilled in the art, for loading ionizable substances onto an ion exchange resin to form the ionizable substance-ion exchange resin complex is to dissolve an acidic or basic, ionizable substance in water, and then mix it with a suitable ion exchange resin. See, for example, U.S. Pat. No. 2,990,332.

Ion exchange resins useful in the practice of the present invention include, but are not limited to, anion exchange resins and cation exchange resins. Preferably, said resins are suitable for human ingestion.

Preferred anion exchange resins include, but are not limited to, styrenic strongly basic anion exchange resins with a quaternary amine functionality having a weight capacity of 0.1 to 15 meq/g, and styrenic weakly basic anion exchange resins with a primary, secondary, or tertiary amine functionality having a weight capacity of 0.1 to 8.5 meq/g, and acrylic or methacrylic strongly basic anion exchange resins with a quaternary amine functionality having a weight capacity of 0.1 to 12 meq/g, and acrylic or methacrylic weakly basic anion exchange resins with a primary, secondary, or tertiary amine functionality having a weight capacity of 0.1 to 12 meq/g, and allylic and vinylic weakly basic anion exchange resins with a primary, secondary, or tertiary amine functionality having a weight capacity of 0.1 to 24 meq/g, that are suitable for human and animal ingestion.

anion exchange resins include, but are not limited to, styrenic anion exchange resins with quaternary amine functionality with weight capacity of 0.1 to 6 meq/g and acrylic anion exchange resins with tertiary amine functionality with weight capacity of 0.1 to 12 meq/g, that are suitable for human and animal ingestion.

Preferred cation exchange resins include, but are not limited to, styrenic strongly acidic cation exchange resins with sulfonic or phosphonic acid functionalities having a weight capacity of 0.1 to 8 meq/g; and styrenic weakly acidic cation exchange resins with carboxylic or phenolic acid functionalities having a weight capacity of 0.1 to 8.5 meq/g; and acrylic or methacrylic weakly acidic cation exchange resins with a carboxylic or phenolic acid functionality with a weight capacity of 0.1 to 14 meq/g, that are suitable for human and animal ingestion.

cation exchange resins include, but are not limited to, styrenic weakly acidic cation exchange resin with a phenolic functionality with a weight capacity of 0.1 to 8.5 meq/g; and a styrenic strongly acidic cation exchange resin with a sulfonic acid functionality with weight capacity of 0.1 to 8 meq/g, or a methacrylic weakly acidic cation exchange resin with a carboxylic acid functionality with weight capacity of 0.1 to 12 meq/g.

Ion exchange resins useful in the practice of this invention have a moisture content between 0% and the water retention capacity of said resin.

Ion exchange resins useful in this invention are in powder or whole bead form.

Strongly acidic and weakly acidic cation exchange resins useful in the practice of this invention are in the acid form or salt form or partial salt form.

Strongly basic anion exchange resins useful in the practice of this invention are in the salt form.

Weakly basic anion exchange resins useful in the practice of this invention are in the free-base form or salt form.

In addition to the controlled substance-ion exchange resin complex, excipients are used in the manufacture of the oral dosage forms of the present invention. Excipients useful in the practice if this invention include, but are not limited to, preservatives, viscosity agents, fillers, lubricants, glidants, disintegrants, binders, coatings, and sensory agents.

Preferred preservatives include, but are not limited to, phenol, alkyl esters of parahydroxybenzoic acid, o-phenylphenol benzoic acid and the salts thereof, boric acid and the salts thereof, sorbic acid and the salts thereof, chlorobutanol, benzyl alcohol, thimerosal, phenylmercuric acetate and nitrate, nitromersol, benzalkonium chloride, cetylpyridinium chloride, methyl paraben, and propyl paraben. Particularly preferred are the salts of benzoic acid, cetylpyridinium chloride, methyl paraben and propyl paraben. The compositions of the present invention generally include from 0-2% preservatives.

Preferred viscosity agents include, but are not limited to, methylcellulose, sodium carboxymethylcellulose, hydroxypropylmethylcellulose, hydroxypropylcellulose, sodium alginate, carbomer, povidone, acacia, guar gum, xanthan gum and tragacanth. Particularly preferred are methylcellulose, carbomer, xanthan gum, guar gum, povidone, sodium carboxymethylcellulose, and magnesium aluminum silicate. Compositions of the present invention include 0-25% viscosity agents.

Preferred fillers include, but are not limited to, lactose, mannitol, sorbitol, tribasic calcium phosphate, dibasic calcium phosphate, compressible sugar, starch, calcium sulfate, dextro and microcrystalline cellulose. The compositions of the present invention contain from 0-75% fillers.

Preferred lubricants include, but are not limited to, magnesium stearate, stearic acid, and talc. The pharmaceutical compositions of the present invention include 0-2% lubricants.

Preferred glidants include, but are not limited to, talc and colloidal silica. The compositions of the present invention include from 0-5% glidants.

Preferred disintegrants include, but are not limited to, starch, sodium starch glycolate, crospovidone, croscarmelose sodium, polacrilin potassium, and microcrystalline cellulose. The pharmaceutical compositions of the present invention include from 0-30% disintegrants.

Preferred binders include, but are not limited to, acacia, tragacanth, hydroxypropylcellulose, pregelatinized starch, gelatin, povidone, hydroxypropylcellulose, hydroxypropylmethylcellulose, methylcellulose, sugar solutions, such as sucrose and sorbitol, and ethylcellulose. The compositions of the present invention include 0.1-10% binders.

Further, the controlled substance-ion exchange resin complex can be coated to produce beneficial effects other than extended release of the controlled substance. The use of coatings for such purposes is well known in the art. See Remington's Pharmaceutical Sciences, 16$^{th}$ Edition, Chapter 90.

Sensory agents useful in the practice of the present invention include, but are not limited to, bitter agents such as denatonium benzoate (Bitrex®), sour agents such as citric acid, pleasant tasting agents such as orange oil, pleasant smelling agents such as mint, and spicy or irritating agents such as capsaicin.

The following non limiting examples illustrate the present invention:

EXAMPLE 1

Preparation of an oxycodone/Bitrex-ion exchange resin complex: 40 g of oxycodone hydrochloride, a Schedule II controlled substance, and 4 g of denatonium benzoate (available as Bitrex® from Macfarlan Smith, Edinburgh, UK) are dissolved in 2000 ml of water. 110 g of a powdered cation exchange resin with sulfonic acid functionality in the sodium form is then added to this solution, and the resulting mixture is shaken for at least 12 hours. The mixture is filtered using a Buchner funnel with a filter capable of retaining particles >0.003 mm. The wet-cake is washed in place with 1000 ml of water. The wet-cake is dried in a vacuum oven at 60° C. for 15 hours, or until constant weight is reached, to give the oxycodone/Bitrex®-ion exchange resin complex.

EXAMPLE 2

Preparation of a hydromorphone-ion exchange resin complex: 40 g of hydromorphone hydrochloride, a Schedule II controlled substance is dissolved in 2000 ml of water. 110 g of a powdered cation exchange resin with sulfonic acid functionality in the sodium form is then added to this solution, and the resulting mixture is shaken for at least 12 hours. The mixture is filtered using a Buchner funnel with a filter capable of retaining particles >0.003 mm. The wet-cake is washed in place with 1000 ml of water. The wet-cake is dried in a vacuum oven at 60° C. for 15 hours, or until constant weight is reached, to give the hydromorphone-ion exchange resin complex.

EXAMPLE 3

Preparation of a Bitrex®-ion exchange resin complex: the procedure of Example 2 is repeated except that the hydromorphone hydrochloride is replaced with 20 g of denatonium benzoate (available as Bitrex® from Macfarlan Smith, Edinburgh, UK).

EXAMPLE 4

Preparation of a tablet of the present invention:

| Composition | |
|---|---|
| Oxycodone/Bitrex-ion exchange resin complex (Example 2) | 320.0 g |
| Lactose (ground) | 35.0 g |
| Colloidal silica | 3.0 g |
| Polyvinylpyrrolidone | 3.0 g |
| Microcrystalline cellulose | 40.0 g |
| Corn starch | 69.0 g |

All the solid ingredients are passed through a 0.6 mm sieve and mix together. The mixture is used to make 9 mm diameter tablets by compression. Each tablet weighs 230 mg and contains an amount of active ingredient equivalent to 40 mg of oxycodone hydrochloride.

EXAMPLE 5

Preparation of a capsule of the present invention: 1500 g of the hydromorphone-ion exchange resin complex obtained in Example 2 is blended with 130 g of Bitrex®-ion exchange resin complex obtained in Example 3. The mixture is filled into 10,000 size 1 capsules. Each capsule contains an amount of active ingredient equivalent to 40 mg of oxycodone hydrochloride.

EXAMPLE 6

A Caucasian male addict, age 48, uses a teaspoonful of a solution of common salt in water to prepare an illicit extract from a 40 mg oxycodone tablet, as prepared in Example 4. After filtering the extract he then injects it intravenously. Because the extraction is inefficient, the non-therapeutic effect, i.e., the high, is not obtained.

EXAMPLE 7

A Caucasian female addict, age 27, weighing 45 kg crushes two 40 mg oxycodone tablets, as prepared in Example 4, into a powder and administers said powder through her nasal cavity. The non-therapeutic effect, i.e. the high, is not obtained.

EXAMPLE 8

At a party a Caucasian male recreational drug user, aged 17, weighing 65 kg is offered two 40 mg oxycodone tablets, as prepared in Example 4, and chews them. The non-therapeutic effect, i.e. the high, is not obtained, and the taste of the tablet is highly objectionable.

EXAMPLE 9

An otherwise healthy Caucasian male, age 48, suffering from post-operational pain related to a severe laceration of a finger follows the instructions of his physician and swallows one oxycodone tablet, as prepared in Example 4. He perceives no bitter taste and experiences the full therapeutic response.

EXAMPLE 10

An Asian female recreational drug user, aged 28, weighing 55 kg, breaks open and empties a hydromorphone capsule, as prepared in Example 5, and uses a shot-glass of a solution of common salt to prepare an illicit extract. She attempts to drink the extract, but the taste is highly objectionable and she does not finish drinking the extract. The non-therapeutic effect, i.e. the high, is not obtained.

I claim:

1. A pharmaceutical comprising, in combination, a resinate and an aversive agent wherein said resinate comprises an ion exchange resin and a drug.

2. The pharmaceutical of claim 1 in which said aversive agent is selected from the group consisting of capsaicin, derivatives of capsaicin, and mixtures thereof.

3. The pharmaceutical of claim 1 in which said drug is a controlled substance.

4. The pharmaceutical of claim 3 in which both said aversive agent and said controlled substance are loaded onto said ion exchange resin.

5. The pharmaceutical of claim 3 in which said aversive agent is loaded onto said ion exchange resin, and said controlled substance is not loaded onto said ion exchange resin.

6. The pharmaceutical of claim 3 in which said controlled substance is loaded onto said ion exchange resin, and said aversive agent is not loaded onto said ion exchange resin.

7. The pharmaceutical of claim 3 in which said controlled substance is loaded onto a first ion exchange resin, and said aversive agent is loaded onto an ion exchange resin different from said first ion exchange resin.

8. The pharmaceutical of claim 1 in the form of a tablet or capsule.

* * * * *

UNITED STATES PATENT AND TRADEMARK OFFICE
CERTIFICATE OF CORRECTION

| | |
|---|---|
| PATENT NO. | : 7,655,256 B2 |
| APPLICATION NO. | : 10/679785 |
| DATED | : February 2, 2010 |
| INVENTOR(S) | : Lyn Hughes |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1571 days.

Signed and Sealed this

Twenty-third Day of November, 2010

David J. Kappos
*Director of the United States Patent and Trademark Office*